United States Patent
Hara et al.

(10) Patent No.: US 11,651,853 B2
(45) Date of Patent: May 16, 2023

(54) INFORMATION PROCESSING APPARATUS, INFORMATION PROCESSING SYSTEM, STORAGE MEDIUM, AND INFORMATION PROCESSING METHOD

(71) Applicant: TOYOTA JIDOSHA KABUSHIKI KAISHA, Toyota (JP)

(72) Inventors: Yusuke Hara, Musashino (JP); Shuhei Aketa, Koto-ku (JP); Toru Yanagida, Nagoya (JP); Shin Sakurada, Toyota (JP); Tae Sugimura, Miyoshi (JP); Yasutaka Ujihara, Meguro-ku (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 284 days.

(21) Appl. No.: 17/027,159

(22) Filed: Sep. 21, 2020

(65) Prior Publication Data
US 2021/0090722 A1    Mar. 25, 2021

(30) Foreign Application Priority Data
Sep. 19, 2019 (JP) .............................. JP2019-170712

(51) Int. Cl.
G16H 40/20 (2018.01)
G16H 40/63 (2018.01)
G16H 40/67 (2018.01)
G16H 10/60 (2018.01)

(52) U.S. Cl.
CPC ............. *G16H 40/20* (2018.01); *G16H 10/60* (2018.01); *G16H 40/63* (2018.01); *G16H 40/67* (2018.01)

(58) Field of Classification Search
CPC ........ G16H 40/20; G16H 40/67; G16H 10/60; G16H 40/63
See application file for complete search history.

(56) References Cited

U.S. PATENT DOCUMENTS

| | | | |
|---|---|---|---|
| 10,684,742 | B2 * | 6/2020 | Okabe et al. |
| 2010/0299177 | A1 * | 11/2010 | Buczkowski et al. |
| 2016/0196387 | A1 * | 7/2016 | Whannel et al. |
| 2016/0342740 | A1 * | 10/2016 | Moore et al. |
| 2017/0300654 | A1 * | 10/2017 | Stein et al. |
| 2019/0361451 | A1 * | 11/2019 | Wilson et al. |
| 2020/0159251 | A1 * | 5/2020 | Iwasaki et al. |
| 2020/0346751 | A1 * | 11/2020 | Horelik et al. |

FOREIGN PATENT DOCUMENTS

| | | | |
|---|---|---|---|
| JP | 2000-116732 A | | 4/2000 |
| RU | 2019/117796 A | * | 6/2019 |

* cited by examiner

*Primary Examiner* — Michael Tomaszewski
*Assistant Examiner* — William T. Monticello
(74) *Attorney, Agent, or Firm* — Oliff PLC

(57) ABSTRACT

An information processing apparatus includes a controller. The controller obtains information about a designated area and information about a medical service target. The controller creates, in accordance with the population distribution in the designated area, a dispatch schedule for dispatching a medical service vehicle capable of dealing with the medical service target to the designated area.

15 Claims, 5 Drawing Sheets

INFORMATION PROCESSING APPARATUS, INFORMATION PROCESSING SYSTEM, STORAGE MEDIUM, AND INFORMATION PROCESSING METHOD

CROSS-REFERENCE TO RELATED APPLICATION

This application claims priority to JP 2019-170712 filed on Sep. 19, 2019, the entire disclosure of which is incorporated herein by reference.

TECHNICAL FIELD

The present disclosure relates to an information processing apparatus, an information processing system, a storage medium, and an information processing method.

BACKGROUND

There is a demand for telemedicine systems in which doctors provide medical services for patients in remote areas. For example, a telemedicine system has been developed in which advanced medical services can be provided at clinics or homes by establishing data communication between medical devices installed in clinics or homes of a patients and a server installed in a hub hospital or the like (refer to PTL 1).

CITATION LIST

Patent Literature

PTL 1: JP 2000-116732 A

SUMMARY

However, with the technology in PTL 1, it is difficult to provide medical services in areas without clinics, and also, providing medical services in the homes of patients requires a significant amount of laborious work for transportation, installation, and dismantling of medical devices. It is therefore difficult to provide many patients with medical services.

The present disclosure has been made in consideration of the circumstances described above, and an object thereof is to provide an information processing apparatus that can provide medical services to many patients in various areas such as areas where doctors are not present.

An information processing apparatus according to an embodiment of the present disclosure is for creating a dispatch schedule for a medical service vehicle and includes a controller configured to obtain information about a designated area and information about a medical service target and create, in accordance with a population distribution in the designated area, a dispatch schedule for dispatching a medical service vehicle capable of dealing with the medical service target to the designated area.

An information processing system according to an embodiment of the present disclosure includes an information processing apparatus, a first terminal apparatus, and a second terminal apparatus. The information processing apparatus is for creating a dispatch schedule for a medical service vehicle and includes a controller configured to obtain information about a designated area and information about a medical service target and create, in accordance with a population distribution in the designated area, a dispatch schedule for dispatching a medical service vehicle capable of dealing with the medical service target to the designated area.

A non-transitory computer-readable storage medium according to an embodiment of the present disclosure stores a program causing an information processing apparatus to execute a process for creating a dispatch schedule for a medical service vehicle. The process includes a step of obtaining information about a designated area and information about a medical service target and a step of creating, in accordance with a population distribution in the designated area, a dispatch schedule for dispatching the medical service vehicle capable of dealing with a medical service target to the designated area.

An information processing method according to an embodiment of the present disclosure is implemented by an information processing apparatus for creating a dispatch schedule for a medical service vehicle. The information processing method includes obtaining information about a designated area and information about a medical service target and creating, in accordance with the population distribution in the designated area, a dispatch schedule for dispatching a medical service vehicle capable of dealing with the medical service target to the designated area.

The information processing apparatus, the information processing system, the storage medium, and the information processing method according to an embodiment of the present disclosure can provide medical services for many patients in various areas.

DETAILED DESCRIPTION

Hereinafter, an embodiment of the present disclosure will be described with reference to the drawings.

Figure 1:
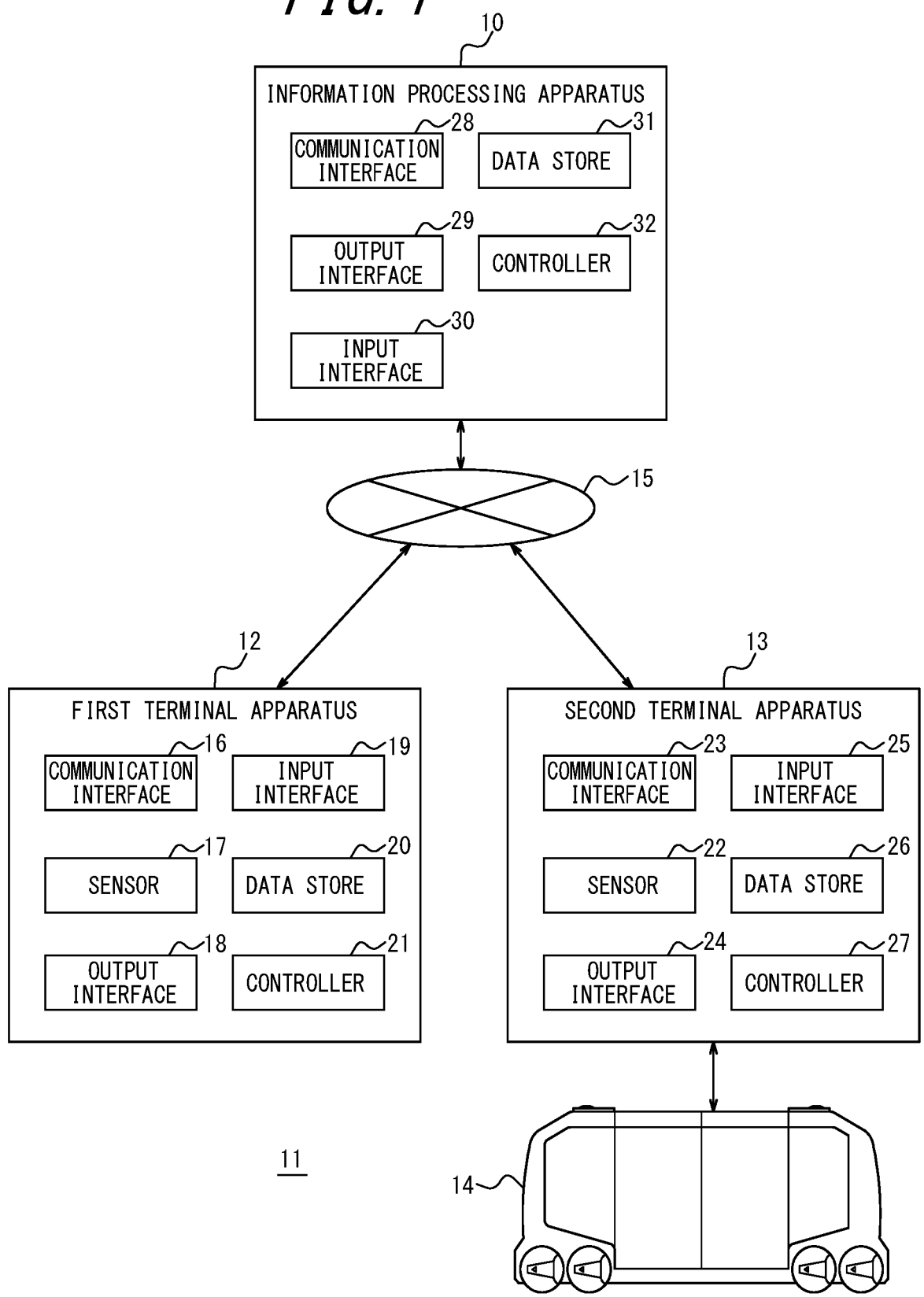
FIG. 1 is a configuration diagram illustrating an overall configuration of an information processing system including an information processing apparatus according to an embodiment of the present disclosure.

An information processing system 11 including an information processing apparatus 10 according to an embodiment of the present disclosure will be outlined with reference to FIG. 1. The information processing system 11 includes a first terminal apparatus 12, a second terminal apparatus 13, and the information processing apparatus 10.

Each of the first terminal apparatus 12 and the second terminal apparatus 13 may be, for example, a general electronic device such as a smartphone or a personal computer (PC), but the first terminal apparatus 12 and the second terminal apparatus 13 are not limited to this example and each may be an electronic device specialized for the information processing system 11. The first terminal apparatus 12 is provided in, for example, a medical facility or the home of a medical service professional. A medical service professional is, for example, a person who is permitted by law to practice medicine, such as a doctor. The second terminal apparatus 13 is installed in a medical service vehicle 14. The information processing apparatus 10 includes one server apparatus or a plurality of server apparatuses that are capable of communicating with each other. While FIG. 1 illustrates one first terminal apparatus 12 and one second terminal apparatus 13 for ease of description, the information processing system 11 may include at one or more first terminal apparatuses 12 and one or more second terminal apparatuses 13.

The first terminal apparatus 12, the second terminal apparatus 13, and the information processing apparatus 10 are communicably connected to a network 15 that includes, for example, a mobile communication network and the Internet. At least part of the information processing system 11 is used for providing a mobility service (Mobility-as-a-Service: MaaS). Service providers can provide a mobility service such as a telemedicine service by using the second terminal apparatus 13 and the medical service vehicle 14.

As an outline of the present embodiment, the information processing apparatus 10 obtains, in response to a request from a state authority, a local authority, or the like, information about a designated area to which a medical service vehicle 14 is to be dispatched and information about a medical service target such as the symptoms of a specific disease that can be treated by medical services in the a medical service vehicle 14. It should be noted that, as used herein, "obtain" denotes obtaining information about a target such as a designated area or a medical service target. The information processing apparatus 10 selects the medical service vehicle 14 that can deal with the medical service target and creates, in accordance with the population distribution in the designated area, a dispatch schedule for dispatching the medical service vehicle 14 to the designated area. It should be noted that, as used herein, "create" denotes creating information on a target such as a dispatch schedule. The information processing apparatus 10 sends the created dispatch schedule to the first terminal apparatus 12. It should be noted that, as used herein, "send" denotes sending information on a target such as a dispatch schedule. The first terminal apparatus 12 presents the received dispatch schedule to a medical service professional. It should be noted that, as used herein, "receive" denotes receiving information on a target such as a dispatch schedule. The information processing apparatus 10 sends the created dispatch schedule or control information based on the dispatch schedule to the second terminal apparatus 13. The control information is information for controlling the medical service vehicle 14 to reach a specific location in a designated area before a medical service start time. The second terminal apparatus 13 causes, in accordance with the received dispatch schedule or the control information, the medical service vehicle 14 to drive to the specific location at which medical services are to be provided. After arrival of the medical service vehicle 14, the information processing apparatus 10 establishes communication between the first terminal apparatus 12 and the second terminal apparatus 13. Through the communication between the second terminal apparatus 13 and the first terminal apparatus 12, the telemedicine service by a medical service professional is received by a patient in the medical service vehicle 14.

Next, the components of the information processing system 11 will be described in detail.

The first terminal apparatus 12 includes a communication interface 16, a sensor 17, an output interface 18, an input interface 19, a data store 20, and a controller 21.

The communication interface 16 includes a communication module that establishes connection with the network 15. For example, the communication interface 16 may include a communication module compliant with mobile communication standards such as the fourth generation (4G) and the fifth generation (5G) standards. In the present embodiment, the first terminal apparatus 12 is connected to the network 15 via the communication interface 16. The communication interface 16 sends and receives various kinds of information through the network 15. When the communication interface 16 sends information through the network 15, the communication interface 16 may add identification information for the first terminal apparatus 12 to the information. The identification information for the first terminal apparatus 12 is information that can be used to uniquely identify the first terminal apparatus 12 in the information processing system 11.

The sensor 17 includes, for example, a sound collection sensor, such as a microphone, and obtains a sound (hereinafter referred to as a "first sound") in the surrounding environment. The sensor 17 may include an imaging sensor, such as a camera, and obtain a subject image (hereinafter referred to as a "first subject image") of the surrounding environment.

The output interface 18 includes at least one interface that outputs information to notify users. For example, the output interface 18 may be, but is not limited to, a display that outputs information as an image or a speaker that outputs information as sound.

The input interface 19 includes at least one interface that detects user inputs. The input interface 19 includes, for example, physical keys, capacitive keys, and/or a touch screen provided in combination with a display of the output interface 18. The touch screen detects a user input designating a relative position on a living body targeted for examination, such as a schematic human body displayed on a display, as a position at which a second sound, a second subject image, or both are obtained in the medical service vehicle 14 equipped with the second terminal apparatus 13 as described later. The second sound and the second subject image are a sound and a subject image obtained by a sensor 22 included in the second terminal apparatus 13.

The data store 20 may be, but is not limited to, a semiconductor memory, a magnetic memory, an optical memory, or the like. The data store 20 may function as, for example, a primary storage unit, an auxiliary storage unit, or a cache memory. The data store 20 stores any information that is used for operation of the first terminal apparatus 12. The data store 20 may store, for example, a system program and an application program. The information stored in the data store 20 may be updated by using, for example, information received from the network 15 via the communication interface 16.

The controller 21 includes at least one processor. In the present embodiment, a "processor" may be, but is not limited to, a general processor or a dedicated processor specialized in a particular processing operation. The dedicated processor may include an application-specific integrated circuit (ASIC). The controller 21 may include a programmable logic device (PLD). The PLD may include a field-programmable gate array (FPGA). The controller 21 controls the entire operation of the first terminal apparatus 12.

When the input interface 19 detects a user input of a designated area to which dispatch of the medical service vehicle 14 and provision of the telemedicine service is desired, the controller 21 controls the communication interface 16 to send information for specifying the designated area to the information processing apparatus 10.

When a dispatch schedule is received from the information processing apparatus 10, the controller 21 stores the dispatch schedule in the data store 20. When the input interface 19 detects a user input requesting output of the dispatch schedule, the controller 21 causes the output interface 18 to output the dispatch schedule.

The controller 21 causes the output interface 18 to output at least one of the second sound and the second subject image received by the communication interface 16. The controller 21 controls the communication interface 16 to send the first sound and the first subject image obtained by the sensor 17 to the second terminal apparatus 13. The controller 21 controls the communication interface 16 to send to the second terminal apparatus 13 a relative position detected by the input interface 19 in accordance with a user input. The controller 21 communicates with the particular second terminal apparatus 13 in accordance with a telemedicine service instruction from the information processing apparatus 10.

For example, when the input interface 19 detects a user input indicating that a medical service is needed at a medical facility and a user input specifying a clinical department, the controller 21 controls the communication interface 16 to send a treatment request including the clinical department to the information processing apparatus 10.

As described above, the second terminal apparatus 13 is installed in the medical service vehicle 14 and, for example, is used in the medical service vehicle 14 for automated driving of the medical service vehicle 14 and the telemedicine service in the medical service vehicle 14. For example, the medical service vehicle 14 may be an autonomous vehicle that can perform automated driving or adaptive cruise control, but is not limited to these and may be any vehicle in which the second terminal apparatus 13 can be installed.

The second terminal apparatus 13 automatically generates control information by using automatic driving control software and sends the control information to the medical service vehicle 14. The medical service vehicle 14 performs vehicle control in accordance with the received control information. For example, the vehicle control may be, but is not limited to, automated driving control. At least part of an application programming interface (API) in which specifications for control information are defined is disclosed to service providers. Service providers can freely develop the automatic driving control software for the second terminal apparatus 13 by programming with the use of the disclosed API. Thus, the service providers can provide any mobility service by installing facilities according to a particular purpose in a space in the cabin of the medical service vehicle 14 and developing automatic driving control software by programming with the use of an API according to the particular purpose.

The second terminal apparatus 13 includes a communication interface 23, the sensor 22, an output interface 24, an input interface 25, a data store 26, and a controller 27.

The communication interface 23 includes a communication module that establishes communication through an in-vehicle network of the medical service vehicle 14, such as a controller area network (CAN), or a dedicated line in the medical service vehicle 14. The communication interface 23 may also include a communication module that establishes a connection with the network 15. In the present embodiment, the second terminal apparatus 13 is connected to on-board devices, such as a control apparatus and a location information acquisition apparatus of the medical service vehicle 14 via the communication interface 23, and communicates information. The second terminal apparatus 13 is also connected to the network 15 via the communication interface 23, or the communication interface 23 and a communication apparatus of the medical service vehicle 14. When the communication interface 23 sends information through the network 15, the communication interface 23 may add identification information for the second terminal apparatus 13 to the information. The identification information for the second terminal apparatus 13 is information that can be used to uniquely identify the second terminal apparatus 13 in the information processing system 11.

The sensor 22 obtains at least one of the second sound and the second subject image of a living body targeted for examination such as the body of a patient.

The sensor 22 includes, for example, a contact-type sound collection sensor such as a chest-piece microphone and receives sound at a part of a patient's body as the second sound while the sensor 22 is in direct contact with the part like a stethoscope. The second sound at a relative position is obtained by receiving sound at the relative position while the contact-type sound collection sensor is in contact with the relative position received from the first terminal apparatus 12.

The sensor 22 may include, for example, a wide-angle camera in which an imaging position is changeable and which obtains, as the second subject image, an enlarged image of a part of the surface of a living body. The sensor 22 may include, for example, an electronic endoscope in which an imaging position is changeable and which obtains as the second subject image a subject image of a lumen, such as the throat, that cannot be easily viewed under interior light. The second subject image at a relative position is obtained by performing imaging in a state in which the wide-angle camera or the front end of an insertion tube of the electronic endoscope is directed toward the relative position received from the first terminal apparatus 12.

The sensor 22 may include, for example, a sound collection sensor, such as a microphone, and receive sound in the medical service vehicle 14. The sensor 22 may include, for example, a camera fixed in the medical service vehicle 14 and obtain subject images in the medical service vehicle 14.

The specific configuration and the functions of the output interface 24 are similar to the configuration and the functions of the output interface 18 of the first terminal apparatus 12. The output interface 24 includes, for example, a display that outputs information in the form of images and outputs the relative position received by the communication interface 23 from the first terminal apparatus 12. The relative position may be, for example, output in a viewable manner in which the relative position is indicated on a schematic drawing of an entire human body by a symbol such as an arrow that indicates a position.

The specific configuration and the functions of the input interface 25 are similar to the configuration and the functions of the input interface 19 of the first terminal apparatus 12.

The specific configuration and the functions of the data store 26 are similar to the configuration and the functions of the data store 20 of the first terminal apparatus 12. The data store 26 stores, for example, any information that is used for operation of the second terminal apparatus 13.

The specific configuration of the controller 27 is similar to the configuration of the controller 21 of the first terminal apparatus 12. The controller 27 controls the entire operation of the second terminal apparatus 13.

When the input interface 25 detects a user input of a medical service target that the medical service vehicle 14, using the second terminal apparatus 13, can deal with, the controller 27 stores the medical service target in the data store 26. The controller 27 selects, in accordance with medical devices and medical items in the medical service vehicle 14 using the second terminal apparatus 13, a medical service target that the medical service vehicle 14 can deal with and stores the medical service target in the data store 26. The controller 27 controls the communication interface 23 to send the medical service target that the medical service vehicle 14 can deal with to the information processing apparatus 10.

When a dispatch schedule is received from the information processing apparatus 10, the controller 27 stores the dispatch schedule in the data store 26. When the input interface 25 detects a user input requesting output of the dispatch schedule, the controller 27 causes the output interface 24 to output the dispatch schedule. The controller 27 generates control information for controlling the medical service vehicle 14 to reach a specific location included in the dispatch schedule before the medical service start time included in the dispatch schedule. The controller 27 may receive, from the information processing apparatus 10, control information generated by the information processing apparatus 10, together with the dispatch schedule.

The controller 27 uses the dispatch schedule in a direct manner or in an indirect manner as control information. The controller 27 sends the control information to the control apparatus of the medical service vehicle 14. When the location of the medical service vehicle 14 detected by the location information acquisition apparatus of the medical service vehicle 14 coincides with the specific location, the controller 27 controls the communication interface 23 to send to the information processing apparatus 10 an indication that the medical service vehicle 14 has reached the specific location.

The controller 27 causes the output interface 24 to output the first sound, the first subject image, and the relative position received by the communication interface 23. The controller 27 controls the communication interface 23 to send to the first terminal apparatus 12 at least one of the second sound and the second subject image obtained at the relative position by the sensor 22. The controller 27 communicates with the particular first terminal apparatus 12 in accordance with a telemedicine service instruction from the information processing apparatus 10.

When information about a particular medical facility is received from the information processing apparatus 10, the controller 27 stores the information about the particular medical facility in the data store 26. The controller 27 notifies the patient receiving the information of the particular medical facility by causing the output interface 24 to output the particular medical facility.

The information processing apparatus 10 includes a communication interface 28, an output interface 29, an input interface 30, a data store 31, and a controller 32.

The specific configuration of the communication interface 28 is similar to the configuration of the communication interface 16 of the first terminal apparatus 12. In the present embodiment, the information processing apparatus 10 is connected to the network 15 via the communication interface 28. The functions of the communication interface 28 are similar to the functions of the communication interface 16 of the first terminal apparatus 12. For example, when the communication interface 28 sends information through the network 15, the communication interface 28 may add identification information for the information processing apparatus 10 to the information. The identification information for the information processing apparatus 10 is information that can be used to uniquely identify the information processing apparatus 10 in the information processing system 11.

The specific configuration and the functions of the output interface 29 are similar to the configuration and the functions of the output interface 18 of the first terminal apparatus 12.

The specific configuration and the functions of the input interface 30 are similar to the configuration and the functions of the input interface 19 of the first terminal apparatus 12.

The specific configuration and the functions of the data store 31 are similar to the configuration and the functions of the data store 20 of the first terminal apparatus 12. The data store 31 stores, for example, any information that is used for operation of the information processing apparatus 10.

The specific configuration of the controller 32 is similar to the configuration of the controller 21 of the first terminal apparatus 12. The controller 32 controls the entire operation of the information processing apparatus 10.

When a medical service target that the medical service vehicle 14 can deal with is received from the second terminal apparatus 13, the controller 32 stores the medical service target in the data store 31 in association with the identification information for the second terminal apparatus 13.

When a designated area and a medical service target are obtained, the controller 32 stores the designated area and the medical service target in the data store 31. When a designated time period is additionally obtained, the controller 32 may store the designated time period in the data store 31 together with the designated area and the medical service target. Dispatch of the medical service vehicle 14 at least within the designated time period is requested. The controller 32 can obtain at least one of the designated area, the designated time period, and the medical service target by user input to the input interface 30. Alternatively, the controller 32 can obtain at least one of the designated area, the designated time period, and the medical service target by receiving the information from the first terminal apparatus 12.

The controller 32 obtains a disease prevalence status for the obtained designated area through the network 15. The controller 32 may obtain the disease prevalence status for the obtained designated area by a user input to the input interface 30.

The controller 32 obtains a population distribution in the obtained designated area. The population distribution in the designated area is represented as, for example, a dot map indicating the number of residents with respect to individual subareas constituting the designated area. The controller 32 may obtain the population distribution in a designated area by acquiring the population distribution through the network 15. The controller 32 may obtain the population distribution in a designated area by retrieving the population distribution from the data store 31 in which population distributions in many areas have been previously stored. The controller 32 may obtain the population distribution in a designated area by a user input to the input interface 30.

The controller 32 selects, in accordance with the obtained medical service target, the medical service vehicle 14 that is to deal with the medical service target. More specifically, the controller 32 retrieves from the data store 31 the identification information for the second terminal apparatus 13 associated with the medical service target. The controller 32 selects the medical service vehicle 14 using the second terminal apparatus 13 of the identification information as the medical service vehicle 14 that is to deal with the medical service target.

The controller 32 creates a dispatch schedule in accordance with the population distribution in the obtained designated area. More specifically, the controller 32 determines, in accordance with the population distribution in the designated area, a specific location at which the medical service vehicle 14 is to park in the designated area and provide a medical service. The determination of the specific location will be explained below.

The controller 32 detects a densely populated area in a designated area. The densely populated area is, for example, an area in which the population per unit area exceeds a threshold. The unit area size can be changed in accordance with the type of the designated area, such as urban, suburban, or rural. The unit area size may be increased as the population of the type of area increases.

The controller 32 detects an available parking location in the detected densely populated area. The available parking location is, for example, a location such as a parking lot, at which parking is not illegal. The controller 32 detects an available parking location in accordance with a map previously stored in the data store 31 or a map received through the network 15. In a case in which an available parking location does not exist within a densely populated area, the controller 32 detects an available parking location close to the densely populated area. The controller 32 determines the detected available parking location as the specific location. In a case in which a plurality of available parking locations are detected, the controller 32 may determine, in consideration of the distance from the center of a densely populated area, ease of parking, traffic safety, and the like, at least one available parking location as the specific location. In a case in which a plurality of densely populated areas are detected within a designated area, the controller 32 may determine a plurality of available parking locations as specific locations.

The controller 32 may determine the specific location in accordance with the type of the disease that is prevalent. The controller 32 may determine the specific location by, for example, detecting an available parking location described above, with respect to a disease that is prevalent, in accordance with the population distribution of a generation which is more likely to contract the disease or is more likely to suffer with severe symptoms of the disease.

The controller 32 may determine a date and time at which the selected medical service vehicle 14 is to be dispatched to the specific location within the obtained designated time period. To determine the date and time, for example, the controller 32 determines a parking time in accordance with the population of the densely populated area corresponding to the specific location. Next, the controller 32 requests, from the second terminal apparatus 13 used by the selected medical service vehicle 14, the dispatch schedule stored in the data store 26 of the second terminal apparatus 13. The controller 32 detects a date and time before which the medical service vehicle 14 can reach the specific location described above and during which the medical service vehicle 14 can be parked for the parking time, wherein the date and time is different from the dates and times for which the medical service vehicle 14 is scheduled to be dispatched in the dispatch schedule received in response to the request. The controller 32 determines the detected date and time as a medical service time for which the medical service vehicle 14 is to be dispatched to the specific location.

The controller 32 creates the dispatch schedule by including the specific location and the medical service time in the dispatch schedule. The controller 32 controls the communication interface 28 to send the dispatch schedule to the second terminal apparatus 13 used by the selected medical service vehicle 14. The controller 32 may generate control information for controlling the medical service vehicle 14 to reach the specific location before the medical service start time and control the communication interface 28 to send the control information together with the dispatch schedule to the second terminal apparatus 13. The controller 32 controls the communication interface 28 to send the same dispatch schedule to the first terminal apparatus 12 corresponding to the second terminal apparatus 13 to which the dispatch schedule is also sent. The first terminal apparatus 12 corresponding to the second terminal apparatus 13 is used by a medical service professional, who can provide a medical service to the medical service target that the medical service vehicle 14 using the second terminal apparatus 13 is able to deal with, to provide a telemedicine service within the medical service time. The controller 32 stores in the data store 31, in an associated manner, the identification information for the first terminal apparatus 12 and the identification information for the second terminal apparatus 13 to both of which the same dispatch schedule is sent.

When a notification indicating that the medical service vehicle 14 has reached the specific location is received from the second terminal apparatus 13, the controller 32 causes the second terminal apparatus 13 and the first terminal apparatus 12 to which the same dispatch schedule has been sent to start communication. Specifically, the controller 32 sends, to the first terminal apparatus 12, an instruction including the identification information for the second terminal apparatus 13 to start communication with the second terminal apparatus 13, and to the second terminal apparatus 13, an instruction including the identification information for the first terminal apparatus 12 to start communication with the first terminal apparatus 12.

When a treatment request is received from the first terminal apparatus 12, the controller 32 stores the treatment request in the data store 31. The controller 32 detects a medical facility that has a clinical department included in the treatment request and is situated in a predetermined range from a designated area. It should be noted that the designated area corresponds to a specific location at which the medical service vehicle 14 using the second terminal apparatus 13 communicating with the first terminal apparatus 12 is to be parked. The controller 32 detects the medical facility through the network 15 or among many medical facilities previously stored in the data store 31. The predetermined range can be changed in accordance with the type of the designated area, such as urban, suburban, or rural. The predetermined range of a particular type of area can be widened as the population of the particular type of area increases. The controller 32 controls the communication interface 23 to send information about the medical facility discovered and specified to the second terminal apparatus 13.

When the input interface 30 detects a user input requesting a suggestion of a candidate area to which the medical service vehicle 14 is able to be dispatched, the controller 32 searches the data store 31 previously storing statistics or the network 15 for statistics regarding the number of doctors and the number of residents in individual areas. For example, a suggestion request of a candidate area may be requested to suggest a candidate area as a designated area in a wide range such as a country, a prefecture, or a city when the wide range is specified. In accordance with the statistics, the controller 32 determines, as a candidate area, an area in which the number of residents to the number of doctors exceeds a threshold. The controller 32 causes the output interface 29 to output the candidate area, so that the controller 32 presents the candidate area as a candidate in accordance with which the user determines a designated area. The controller 32 may present a candidate area in accordance with past dispatch records of the medical service vehicle 14. The controller 32 may suggest a candidate area in accordance with the status of a war or a conflict occurring in the area.

Figure 2:
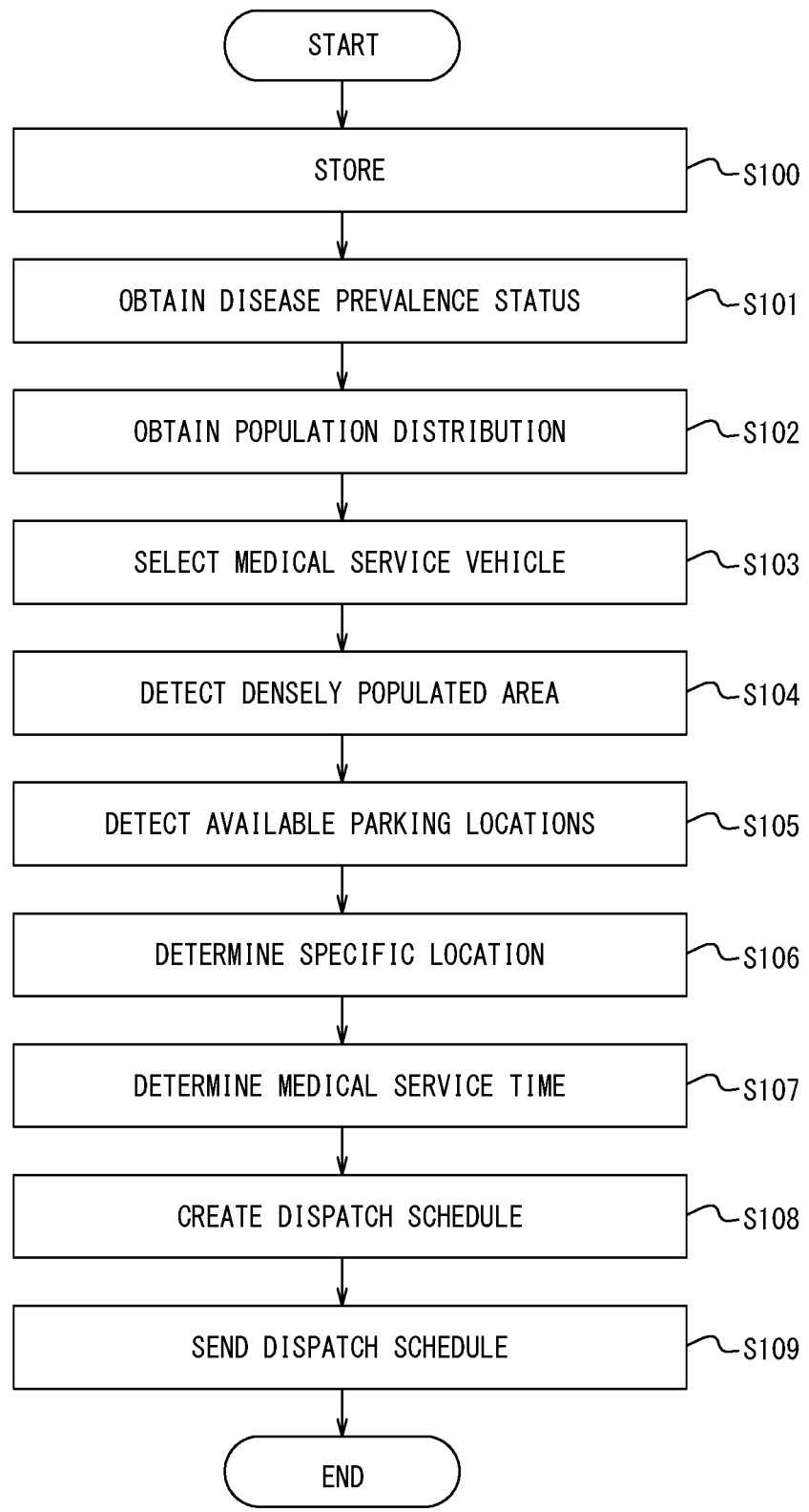
FIG. 2 is a flowchart of dispatch schedule creation processing performed by a controller of the information processing apparatus in FIG. 1.

Next, dispatch schedule creation processing performed by the controller 32 of the information processing apparatus 10 in the present embodiment will be described with reference to the flowchart of FIG. 2. The dispatch schedule creation processing starts when, for example, a designated area and the like are obtained.

In step S100, the controller 32 stores the obtained designated area, a medical service target, and a designated time period in the data store 31. After the information is stored, the process proceeds to step S101.

In step S101, the controller 32 obtains a disease prevalence status for the designated area stored in the data store 31 in step S100. After the disease prevalence status is obtained, the process proceeds to step S102.

In step S102, the controller 32 obtains a population distribution in the designated area stored in the data store 31 in step S100. After the population distribution is obtained, the process proceeds to step S103.

In step S103, the controller 32 selects the medical service vehicle 14 that can deal with the medical service target stored in the data store 31 in step S100. The controller 32 stores in the data store 31 identification information for the second terminal apparatus 13 used by the selected medical service vehicle 14. After the medical service vehicle 14 is selected, the process proceeds to step S104.

In step S104, the controller 32 detects, in accordance with the population distribution obtained in step S102, a densely populated area with respect to a generation corresponding to the disease prevalence status obtained in step S101. After the densely populated area is detected, the process proceeds to step S105.

In step S105, the controller 32 detects available parking locations within or close to the densely populated area detected in step S104. After the available parking locations are detected, the process proceeds to step S106.

In step S106, the controller 32 determines, as a specific location, at least one available parking location out of the available parking locations detected in step S105. After the specific location is determined, the process proceeds to step S107.

In step S107, the controller 32 determines a medical service time for the specific location within the designated time period stored in the data store 31 in step S100. After the medical service time is determined, the process proceeds to step S108.

In step S108, the controller 32 creates a dispatch schedule including the specific location determined in step S106 and the medical service time determined in step S107. The controller 32 stores the dispatch schedule in the data store 31. After the dispatch schedule is created, the process proceeds to step S109.

In step S109, the controller 32 controls the communication interface 28 to send the dispatch schedule created in step S108 to the second terminal apparatus 13 used by the medical service vehicle 14 selected in step S103. The controller 32 controls the communication interface 28 to send the same dispatch schedule to the first terminal apparatus 12 corresponding to the second terminal apparatus 13. The controller 32 stores in the data store 31, in an associated manner, the identification information for the first terminal apparatus 12 and the identification information for the second terminal apparatus 13 to both of which the same dispatch schedule is sent. After the dispatch schedule is sent, the dispatch schedule creation processing is ended.

Figure 3:
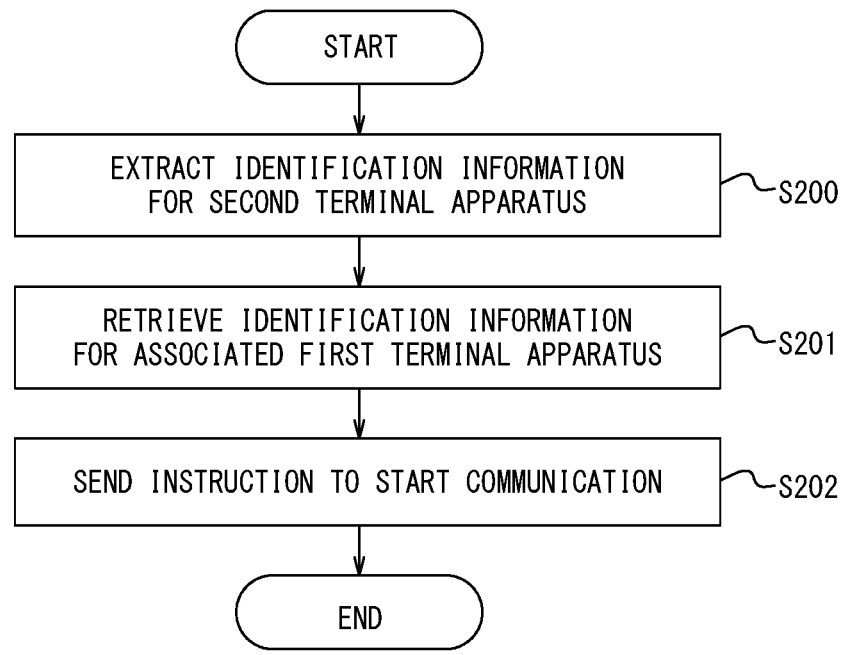
FIG. 3 is a flowchart of communication initiation processing performed by the controller of the information processing apparatus in FIG. 1.

Next, communication initiation processing performed by the controller 32 of the information processing apparatus 10 in the present embodiment will be described with reference to a flowchart in FIG. 3. The communication initiation processing is started when, for example, a notification indicating arrival at a specific location is received from the second terminal apparatus 13.

In step S200, the controller 32 extracts identification information for the second terminal apparatus 13 from the received notification. After the identification information for the second terminal apparatus 13 is extracted, the process proceeds to step S201.

In step S201, the controller 32 retrieves from the data store 31 identification information for the first terminal apparatus 12 associated with the identification information for the second terminal apparatus 13 extracted in step S200. After the identification information for the first terminal apparatus 12 is retrieved, the process proceeds to step S202.

In step S202, the controller 32 controls the communication interface 28 to send, to the second terminal apparatus 13 of the identification information extracted in step S200, an instruction to start communication, together with the identification information for the first terminal apparatus 12 retrieved in step S201. The controller 32 controls the communication interface 28 to also send, to the first terminal apparatus 12 of the identification information retrieved in step S201, an instruction to start communication, together with the identification information for the second terminal apparatus 13 extracted in step S200. After the instruction and the identification information are sent, the communication initiation processing is ended.

Figure 4:
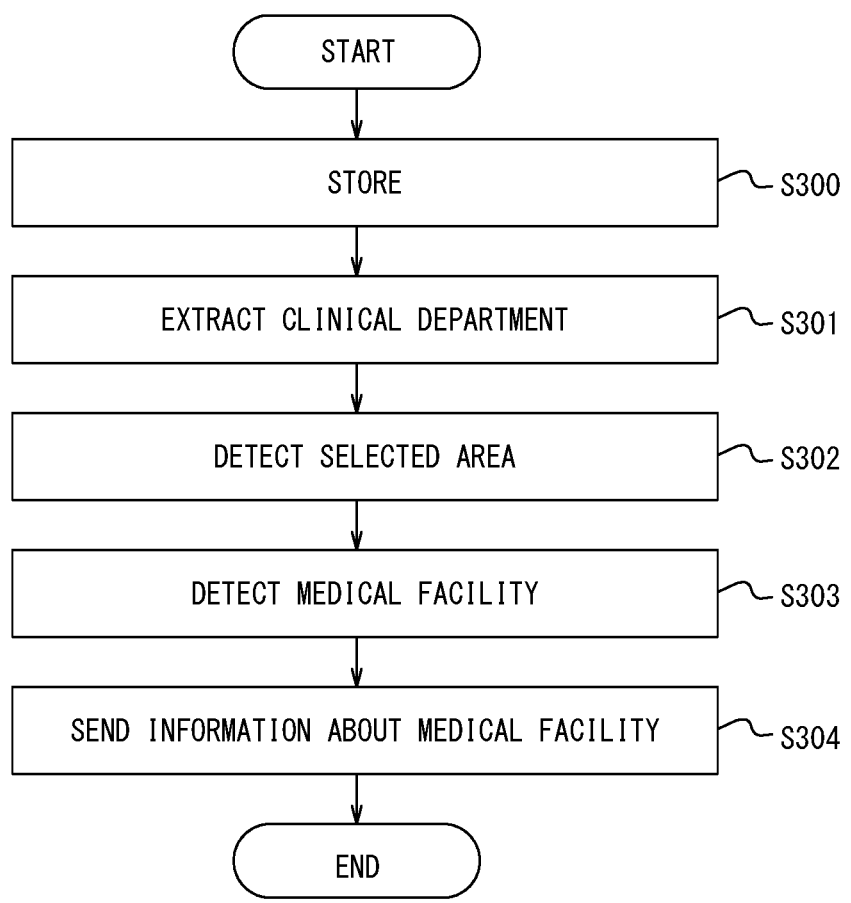
FIG. 4 is a flowchart of referral processing performed by the controller of the information processing apparatus in FIG. 1.

Next, referral processing performed by the controller 32 of the information processing apparatus 10 in the present embodiment will be described with reference to a flowchart in FIG. 4. The referral processing is started when, for example, a treatment request is received from the first terminal apparatus 12.

In step S300, the controller 32 stores the received treatment request in the data store 31. After the treatment request is stored, the process proceeds to step S301.

In step S301, the controller 32 extracts a clinical department from the treatment request stored in the data store 31 in step S300. After the clinical department is extracted, the process proceeds to step S302.

In step S302, the controller 32 extracts identification information for the first terminal apparatus 12 from the treatment request stored in the data store 31 in step S300. The controller 32 retrieves identification information for the second terminal apparatus 13 associated with the identification information for the first terminal apparatus 12 from the data store 31. In accordance with the identification information for the second terminal apparatus 13, the controller 32 recognizes a specific location at which the medical service vehicle 14 using the second terminal apparatus 13 is to park according to a dispatch schedule stored in the data store 31. The controller 32 detects a designated area corresponding to the specific location. After the designated area is detected, the process proceeds to step S303.

In step S303, the controller 32 detects a medical facility that has the clinical department extracted in step S301 and that is situated within a predetermined range from the designated area detected in step S302. After the medical facility is detected, the process proceeds to step S304.

In step S304, the controller 32 controls the communication interface 28 to send information about the medical facility detected in step S303 to the second terminal apparatus 13 of the identification information retrieved in step S302. After the information about the medical facility is sent, the referral processing is ended.

Figure 5:
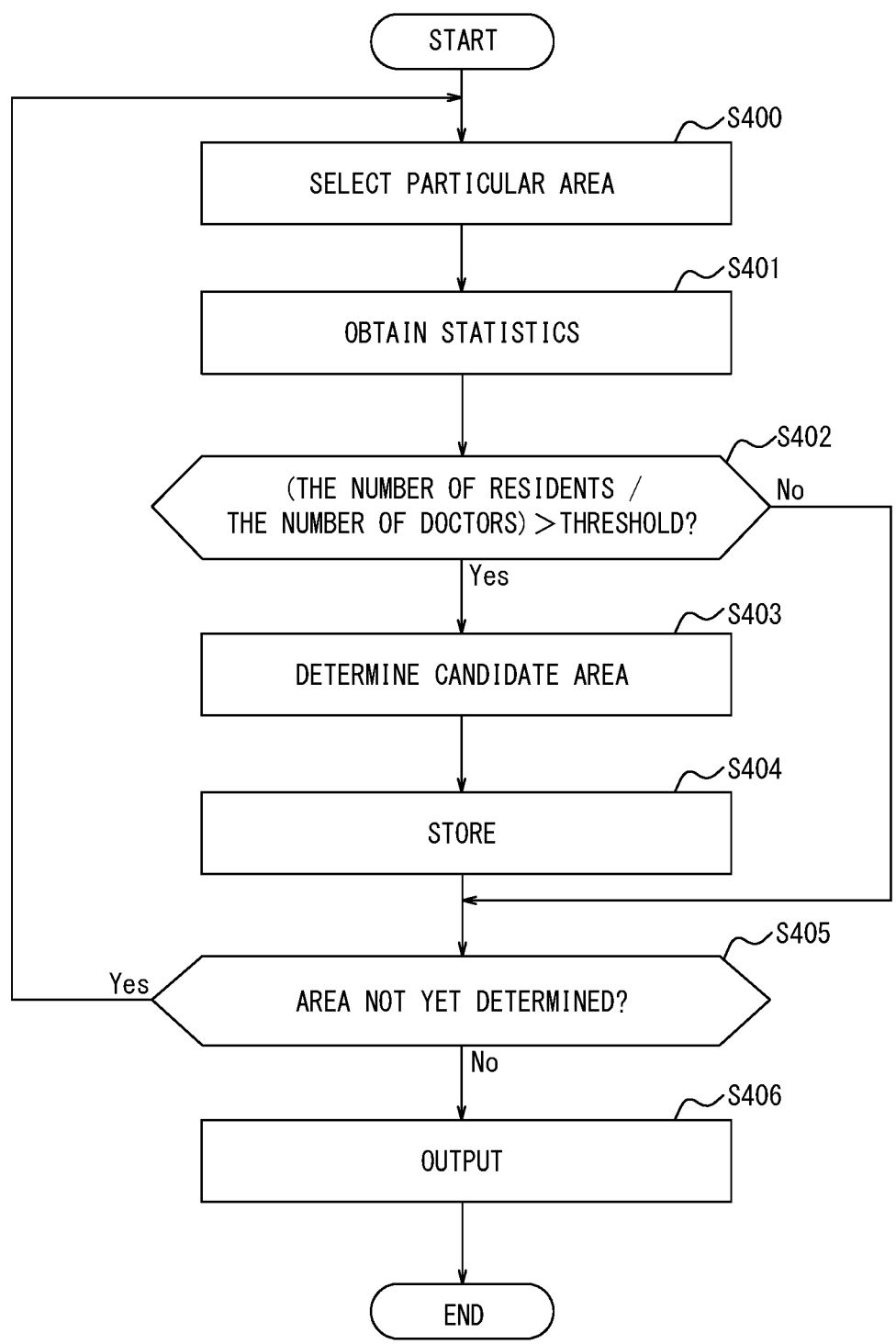
FIG. 5 is a flowchart of suggestion processing performed by the controller of the information processing apparatus in FIG. 1.

Next, suggestion processing performed by the controller 32 of the information processing apparatus 10 in the present embodiment will be described with reference to a flowchart in FIG. 5. The suggestion processing is started when, for example, the input interface 30 detects a user input requesting suggestion of a candidate area together with designation of a wide range.

In step S400, the controller 32 selects a particular area in the designated range. After the particular area is selected, the process proceeds to step S401.

In step S401, the controller 32 obtains, through the network 15 or from the data store 31, statistics regarding the number of doctors and the number of residents in the particular area selected in step S401. After the statistics are obtained, the process proceeds to step S402.

In step S402, in accordance with the statistics obtained in step S401, the controller 32 determines whether the number of residents to the number of doctors exceeds a threshold. In a case in which the number of residents to the number of doctors exceeds the threshold, the process proceeds to step S403. In a case in which the number of residents to the number of doctors does not exceed the threshold, the process proceeds to step S405.

In step S403, the controller 32 determines the particular area selected in step S400 as a candidate area. After the candidate area is determined, the process proceeds to step S404.

In step S404, the controller 32 stores in the data store 31 the candidate area determined in step S403. After the candidate area is stored, the process proceeds to step S405.

In step S405, the controller 32 determines whether there is an area for which it has not yet been determined whether the area is a candidate area within the designated range. In a case in which there is such an area, the process returns to step S400. In a case in which there is no such area, the process proceeds to step S406.

In step S406, the controller 32 causes the output interface 29 to output the candidate area stored in the data store 31 in step S404. After the candidate area is output, the suggestion processing is ended.

The information processing apparatus 10 according to the present embodiment configured as described above obtains information about a designated area and information about a medical service target and creates, in accordance with the population distribution in the designated area, a dispatch schedule for dispatching a medical service vehicle 14 capable of dealing with the medical service target to the designated area. With this configuration, the information processing apparatus 10 can efficiently dispatch a medical service vehicle 14 having equipment capable of treating a symptom as a medical service target to, for example, an area without doctors such as a village without doctors or a conflict area, in response to, for example, a request from a state authority, a local authority, or the like. Thus, the information processing apparatus 10 can provide a telemedicine service in various areas by using the medical service vehicle 14, which functions as a clinic, and as a result, it is possible to provide many patients with medical services.

Furthermore, the information processing apparatus 10 according to the present embodiment creates the dispatch schedule also in accordance with a disease prevalence status. With this configuration, the information processing apparatus 10 can dispatch the medical service vehicle 14 to areas in which providing medical services will have greater effect. Thus, the information processing apparatus 10 can decrease the number of affected patients in a designated area.

Moreover, the information processing apparatus 10 according to the present embodiment receives information about a designated area from the first terminal apparatus 12. With this configuration, by using the information processing apparatus 10, a medical service professional who desires to provide medical services in a particular area can input the particular area as a designated area. Thus, the information processing apparatus 10 enables the telemedicine service to be provided in the particular area desired by the medical service professional.

Further, the information processing apparatus 10 according to the present embodiment presents a candidate area, in accordance with statistics regarding the number of doctors and the number of residents with respect to individual areas, to which the medical service vehicle 14 can be dispatched, to determine the designated area. With this configuration, the information processing apparatus 10 not only waits for an area to be specified to dispatch the medical service vehicle 14 but also can cause the user to recognize a candidate area to which the medical service vehicle 14 is desired to be dispatched and provide information useful for suggestions to local authorities or the like.

Furthermore, when a notification indicating that the medical service vehicle 14 has reached a specific location is received from the second terminal apparatus 13, the information processing apparatus 10 according to the present embodiment causes the first terminal apparatus 12 and the second terminal apparatus 13 to start communication between the first terminal apparatus 12 and the second terminal apparatus 13. With this configuration, the information processing apparatus 10 initiates communication when medical services can be provided, and as a result, it is possible to hinder unnecessary communication.

Moreover, when a treatment request is received from the first terminal apparatus 12, the information processing apparatus 10 according to the present embodiment sends, to the second terminal apparatus 13, information about a particular medical facility that has a clinical department included in the treatment request and that is situated within a predetermined range from the designated area. With this configuration, the information processing apparatus 10 can refer a patient to whom it is difficult to provide medical services in the medical service vehicle 14 to a medical facility capable of providing medical services to the patient.

Further, the information processing apparatus 10 according to the present embodiment changes the predetermined range in accordance with the designated area. With this configuration, the information processing apparatus 10 can detect an appropriate number of medical facilities in a normal condition in which the distance from a designated area to a nearby medical facility varies depending on the type of the designated area.

While the present disclosure has been described with reference to the accompanying drawings and the examples, it should be noted that various changes and modifications based on the present disclosure may be easily made by those skilled in the art. It should be noted that these changes and modifications are therefore embraced in the scope of the present disclosure. For example, the functions and the like included in the constituents and steps may be rearranged in a logically consistent manner; a plurality of means or steps may be combined together or divided.

For example, part of the processing operation performed by the information processing apparatus 10, the first terminal apparatus 12, and the second terminal apparatus 13 in the embodiment described above may be carried out by another apparatus.

In particular, part of the processing operation performed by the information processing apparatus 10 may be carried out by the first terminal apparatus 12. Alternatively, the information processing apparatus 10 may be integrated with the first terminal apparatus 12.

Furthermore, for example, a general electronic device such as a smartphone or a computer may be configured to function as the information processing apparatus 10, the first terminal apparatus 12, or the second terminal apparatus 13 according to the embodiment described above. Specifically, a program in which details of processing for implementing the function of, for example, the information processing apparatus 10 according to the embodiment are written is stored in a memory of an electronic device; a processor of the electronic device reads and runs the program. Thus, the disclosure according to the present embodiment may be implemented as a program that can be run by a processor. The program may be downloaded through the network 15; or the program may be stored in a portable non-transitory recording/storage medium readable by electronic devices and the program may be read from the medium by an electronic device.

The invention claimed is:

1. An information processing system comprising:
a terminal apparatus;
a medical service vehicle; and
an information processing apparatus comprising:
    a memory configured to store respective medical service targets that medical service vehicles can deal with, in association with identification information for respective terminal apparatuses installed in the medical service vehicles;
    a controller configured to:
        receive, through a network, information about a designated area and information about a designated medical service target;
        receive through the network, or retrieve from information about population distributions in a plurality of areas previously stored in the memory, information about a population distribution in the designated area;
        detect a densely populated area in which a population per unit area exceeds a threshold within the designated area in accordance with the information about the population distribution in the designated area;
        detect a specific location that is an available parking location within or around the densely populated area in accordance with a map received through the network or previously stored in the memory;
        determine a parking time in accordance with a population of the densely populated area;
        create a dispatch schedule for dispatching a medical service vehicle capable of dealing with the designated medical service target to the designated area, the dispatch schedule including the specific location and the parking time;
        read identification information stored in the memory in association with the designated medical service target; and
        transmit the dispatch schedule through the network to the terminal apparatus, which corresponds to the identification information, wherein
    the terminal apparatus is configured to:
        receive, through the network, the dispatch schedule from the information processing apparatus; and
        generate control information for controlling the medical service vehicle to reach the specific location included in the dispatch schedule and park during the parking time included in the dispatch schedule, and
    the medical service vehicle is configured to perform automated driving in accordance with the control information.

2. The information processing system according to claim 1, wherein
the controller is configured to create the dispatch schedule in accordance with a disease prevalence status.

3. The information processing system according to claim 1, wherein
the controller is configured to present, in accordance with statistics regarding a number of doctors and a number of residents with respect to individual areas, a candidate area, to which the medical service vehicle is able to be dispatched, to determine the designated area.

4. The information processing system according to claim 1, wherein
the controller is configured to obtain the information about the designated area by receiving the information about the designated area from a second terminal apparatus.

5. The information processing system according to claim 4, wherein
the controller is configured to, when a notification indicating that the medical service vehicle has reached a specific location in the designated area is received from the terminal apparatus, which performs a telemedicine service by establishing communication with the second terminal apparatus, perform control for initiating communication between the second terminal apparatus and the terminal apparatus.

6. The information processing system according to claim 5, wherein
the controller is configured to, when a treatment request at a medical facility is received from the second terminal apparatus, send, to the terminal apparatus, information about a particular medical facility that has a clinical department included in the treatment request and that is situated within a predetermined range from the designated area.

7. The information processing system according to claim 6, wherein
the controller is configured to change the predetermined range in accordance with the designated area.

8. An information processing method comprising:
causing an information processing apparatus to receive, through a network, information about a designated area and information about a designated medical service target;

receive through the network, or retrieve from information about population distributions in a plurality of areas previously stored in a memory of the information processing apparatus, information about a population distribution in the designated area;

detect a densely populated area in which a population per unit area exceeds a threshold within the designated area in accordance with the information about the population distribution in the designated area;

detect a specific location that is an available parking location within or around the densely populated area in accordance with a map received through the network or previously stored in the memory;

determine a parking time in accordance with a population of the densely populated area;

create a dispatch schedule for dispatching a medical service vehicle capable of dealing with the designated medical service target to the designated area, the dispatch schedule including the specific location and the parking time;

read identification information stored in the memory in association with the designated medical service target;

transmit the dispatch schedule through the network to a terminal apparatus, which corresponds to the identification information;

causing the terminal apparatus to generate control information for controlling a medical service vehicle to reach the specific location included in the dispatch schedule and park during the parking time included in the dispatch schedule; and causing the medical service vehicle to perform automated driving in accordance with the control information.

9. The information processing method according to claim 8, wherein
the information processing apparatus creates the dispatch schedule also in accordance with a disease prevalence status.

10. The information processing method according to claim 8, further comprising:
the information processing apparatus presents, in accordance with statistics regarding a number of doctors and a number of residents with respect to individual areas, a candidate area, to which the medical service vehicle is able to be dispatched, to determine the designated area.

11. The information processing method according to claim 8, wherein
the information processing apparatus obtains the information about the designated area by receiving the information about the designated area from a second terminal apparatus.

12. The information processing method according to claim 11, wherein
when a notification indicating that the medical service vehicle has reached a specific location in the designated area is received from the terminal apparatus, which provides a telemedicine service by establishing communication with the second terminal apparatus, the information processing apparatus initiates communication between the second terminal apparatus and the terminal apparatus.

13. The information processing method according to claim 12, wherein
when receiving a treatment request at a medical facility from the second terminal apparatus, the information processing apparatus sends, to the terminal apparatus, information about a particular medical facility that has a clinical department included in the treatment request and that is situated within a predetermined range from the designated area.

14. The information processing system according to claim 1, wherein the controller is configured to
receive, through the network, the information about the designated area from a another terminal apparatus for use of a medical service professional; and
after transmitting, through the network, the dispatch schedule to the terminal apparatus corresponding to the identification information, and upon receiving, through the network, a notification indicating that the medical service vehicle has reached the specific location from the terminal apparatus corresponding to the identification information, transmit, through the network, an instruction to start communication with the terminal apparatus corresponding to the identification information and an instruction to start communication with the other terminal apparatus that includes second identification information for the other terminal apparatus, to the other terminal apparatus and the terminal apparatus, respectively, thereby causing the other terminal apparatus and the terminal apparatus to initiate communication with each other for a telemedicine service, wherein the terminal apparatus is for use of a patient.

15. The information processing system according to claim 1, further comprising
a second terminal apparatus configured to:
receive, through the network, the dispatch schedule from the information processing apparatus; and
display the dispatch schedule on a display in response to a user input requesting output of the dispatch schedule.

* * * * *